(12) United States Patent
Wang et al.

(10) Patent No.: US 12,310,797 B2
(45) Date of Patent: May 27, 2025

(54) ORAL TREATMENT PROTECTIVE OPERATION DEVICE

(71) Applicant: Chongqing Medical University, Chongqing (CN)

(72) Inventors: Shengguo Wang, Chongqing (CN); Shu Zhang, Chongqing (CN); Yunying Wang, Chongqing (CN); Huizhe Huang, Chongqing (CN); Qian Li, Chongqing (CN); Tingyue Deng, Chongqing (CN); Jing Lu, Chongqing (CN)

(73) Assignee: Chongqing Medical University, Chongqing (CN)

( * ) Notice: Subject to any disclaimer, the term of this patent is extended or adjusted under 35 U.S.C. 154(b) by 434 days.

(21) Appl. No.: 17/781,822

(22) PCT Filed: Mar. 20, 2020

(86) PCT No.: PCT/CN2020/080426
§ 371 (c)(1),
(2) Date: Jun. 2, 2022

(87) PCT Pub. No.: WO2021/179346
PCT Pub. Date: Sep. 16, 2021

(65) Prior Publication Data
US 2023/0009068 A1    Jan. 12, 2023

(30) Foreign Application Priority Data
Mar. 10, 2020    (CN) .......................... 202010162605.6

(51) Int. Cl.
*A61B 90/00*    (2016.01)
*A61B 1/24*    (2006.01)
(Continued)

(52) U.S. Cl.
CPC ................ *A61B 90/05* (2016.02); *A61B 1/24* (2013.01); *A61B 1/247* (2013.01); *A61G 15/10* (2013.01)

(58) Field of Classification Search
CPC ........... A61B 90/05; A61B 1/24; A61B 1/247; A61G 10/00; A61G 10/005; A61G 10/02;
(Continued)

(56) References Cited

U.S. PATENT DOCUMENTS 5,299,582 A * 4/1994 Potts ...................... A61B 90/40
128/849
10,251,801 B2 * 4/2019 Breegi .................. A61B 90/30
2002/0069869 A1 6/2002 Farmer

FOREIGN PATENT DOCUMENTS

CN    202036359 U    11/2011
CN    106420065 A    2/2017
(Continued)

OTHER PUBLICATIONS

Merriam-Webster Online Dictionary, definition of "butt joint". (Year: 2024).*

*Primary Examiner* — Keri J Nelson
(74) *Attorney, Agent, or Firm* — Calderon Safran & Wright PC; Corinne Marie Pouliquen

(57) ABSTRACT

An oral treatment protective operation device, comprising a protective cover assembly and a suspension support connected thereto. The protective cover assembly comprises a transparent protective cover; the protective cover is provided with a soft sealing sleeve in butt-joint with a patient's mouth and a connector connecting a strong suction pipe; the left side and the right side of the protective cover are provided with operation windows; the opening parts of the operation windows are provided with arc-shaped sliding plates, which are provided with circular operation holes; the operation holes are connected to soft arm sleeves; a concave part is
(Continued)

formed on the side of the protective cover facing a doctor, and an angle-adjustable magnifying lens is arranged in the concave part; and the suspension support comprises a vertical-deflection adjusting rod, a transverse connecting rod and a connecting lock sleeve, and further comprises a stay cable or a stay bar.

20 Claims, 4 Drawing Sheets

(51) Int. Cl.
*A61B 1/247* (2006.01)
*A61G 15/10* (2006.01)

(58) Field of Classification Search
CPC .... A61G 10/023; A61G 10/026; A61G 10/04; A61G 15/10
See application file for complete search history.

(56) References Cited

FOREIGN PATENT DOCUMENTS

| | | |
|---|---|---|
| CN | 209695163 U | 11/2019 |
| CN | 111214309 A | 6/2020 |
| CN | 111227978 A | 6/2020 |
| DE | 2944397 A1 | 5/1981 |
| JP | 2000185071 A | 7/2000 |

* cited by examiner

ORAL TREATMENT PROTECTIVE OPERATION DEVICE

CROSS-REFERENCE TO RELATED APPLICATIONS AND CLAIM TO PRIORITY

This application is a national stage application of International Application No. PCT/CN2020/080426 filed Mar. 20, 2020, which claims priority to Chinese Patent Application No. 202010162605.6 filed Mar. 10, 2020, the disclosures of which are incorporated herein by reference and to which priority is claimed.

FIELD OF THE INVENTION

The present disclosure relates to an oral medical device, and in particular relates to a protective operation device.

BACKGROUND OF THE INVENTION

Oral treatment is prone to aerosol transmission due to its treatment space and the particularity of the device. Firstly, the close contact between the patient and medical staff provides convenience to the spread of aerosols; secondly, the water mist produced by a high-speed air turbine handpiece, an ultrasonic scaler, piezosurgery and a three-way air-water syringe tip used for dental treatment is mixed with blood and saliva of the patient, which is prone to generating aerosol to contaminate the surrounding air and surfaces of objects. Meanwhile, coughing of the patient is easily caused in the treatment process of the patient, which is one of risk factors of generating aerosol easily. At present, the pathogenic microorganisms known to be transmitted by the aerosol include novel coronavirus, SARS coronavirus, hepatitis B virus, hepatitis C virus, and human immunodeficiency virus (HIV). In addition, except for the aerosol transmission, there are also routes of droplet transmission in the treatment of oral diseases.

As there is a possibility of infection by viruses transmitted by the aerosol and droplets between medical staff and adjacent patients during oral treatment, the prevention of cross infection during oral treatment is a technical problem worth studying.

Moreover, the treatment operation is more difficult for the doctor due to poor light in the oral cavity and narrow operation visual field, therefore, it is a technical problem to improve the treatment operation visual field of the doctor on the basis of preventing cross infection in the oral treatment operation.

SUMMARY OF THE INVENTION

To this end, an objective of the present disclosure is to provide an oral treatment protective operation device, which not only solves the technical problem of cross infection caused by diffusion of virus-containing aerosol and droplets to the surrounding environment, but also solves the technical problem of how to improve the treatment operation visual field of a doctor.

To solve above technical problems, the following technical solutions are adopted by the present disclosure:

an oral treatment protective operation device, comprising a protective cover assembly and a suspension support; wherein the protective cover assembly comprises a transparent protective cover, the lower part of the protective cover is provided with a soft sealing sleeve in butt-joint with a patient's mouth, the left side and the right side of the protective cover are provided with operation holes for entry of hands, and the operation holes are connected to soft arm sleeves; the arm sleeves are provided with a first side pipe for penetration of a mouth mirror and a second side pipe for penetration of a weak suction pipe respectively; the protective cover is further provided with a connector connecting to a strong suction pipe; and the top of the protective cover is further provided with a spherical hinge with a locking mechanism;

the suspension support comprises a vertical-deflection adjusting rod, a transverse connecting rod, and a connecting lock sleeve, and further comprises a stay bar or a stay cable; one end of the vertical-deflection adjusting rod is connected to the spherical hinge on the protective cover, and the other end of the vertical-deflection adjusting rod is connected to the transverse connecting rod through a hinge joint with the locking mechanism; the connecting lock sleeve comprises a sleeve body which is provided with a transverse sleeve hole and a vertical sleeve hole; the connecting lock sleeve further comprises a first threaded handle arranged on the transverse sleeve hole and a second threaded handle arranged on the vertical sleeve hole; the transverse connecting rod is arranged in the transverse sleeve hole and in sliding fit with the transverse sleeve hole; the vertical sleeve hole of the connecting lock sleeve is used for being connected to a stand column of a treatment chair for stomatology department; and the stay bar or the stay cable is configured for connecting the vertical-deflection adjusting rod to the stand column of the treatment chair for the stomatology department.

Further, a concave part which is concave towards the inner side of the protective cover is formed on a side of the protective cover facing a doctor, and a hemispherical recess in which a magnifying lens is arranged is formed in the concave part; an annular groove is formed at an opening part of the hemispherical recess; and a rubber ring is arranged on a circumferential surface of magnifying lens, the magnifying lens is connected to the annular groove through the rubber ring, and the magnifying lens is rotatable around a diameter of the annular groove.

Further, each of the left side and the right side of the protective cover is provided with an operation window, an opening part of the operation window is provided with an arc-shaped guide groove, and an arc-shaped sliding plate is arranged in the guide groove, which arc-shaped sliding plate is in sliding fit with the guide groove; the operation hole on the left side of the protective cover is provided on the arc-shaped sliding plate at the left side, and the operation hole on the right side of the protective cover is provided on the arc-shaped sliding plate at the right side.

Further, the lower part of the protective cover is provided with a tubular joint in butt-joint with the soft sealing sleeve, and the soft sealing sleeve is in detachable butt-joint with the tubular joint.

Further, the vertical-deflection adjusting rod is a telescopic rod having a length capable of being telescopically adjusted.

Further, the vertical-deflection adjusting rod is further provided with a clamping plate for fixing the strong suction pipe.

Further, the vertical-deflection adjusting rod is further provided with a connecting plate for stay cable.

Further, the suspension support further comprises a positioning sleeve configured for connecting to the stand column of the treatment chair for the stomatology department and located below the connecting lock sleeve.

The present disclosure has the beneficial effects that:

1. during use of the oral treatment protection operation device of the present disclosure, the protective cover assembly is connected to the suspension support, the suspension support is connected to the stand column of the treatment chair for the stomatology department, and the soft sealing sleeve of the protective cover assembly is in butt-joint with the mouth of a patient; the soft sealing sleeve is in comfortable contact with the skin around the lips without causing discomfort; and the protective cover assembly is connected to the suspension support, thus the protective cover assembly does not cause oppression discomfort to the patient. In the course of treatment, the transparent protective cover cannot affect the visual field of a doctor, the hands of the doctor enter the protective cover from the arm sleeves at two sides of the protective cover, and the sealing is improved through the fitting of the arm sleeves and the arms; and in the course of treatment, the aerosol and droplets generated by the patient are sucked away by the strong suction pipe which is connected to the protective cover, thus solving the problem of cross infection caused by diffusion of the aerosol and droplets to the surrounding environment.

2. In accordance with the oral treatment protection operation device of the present disclosure, the concave part is formed on the side of the protective cover facing the doctor, and the magnifying lens is arranged in the concave part; and an angle of the magnifying lens can be adjusted according to demands of the doctor, thus the doctor can conveniently observe internal conditions of the oral cavity clearly through the magnifying lens, and the operation visual field of the doctor is improved.

3. In accordance with the oral treatment protection operation device of the present disclosure, it is guaranteed that the position of the protective cover can be adjusted conveniently and flexibly through the angle-adjustable vertical-deflection adjusting rod, a hinge structure of the vertical-deflection adjusting rod and the transverse connecting rod, and a spherical hinge structure connecting the protective cover and the vertical-deflection adjusting rod, thus the protective cover can be in rapid butt-joint with the mouth of the patient during use.

4. In accordance with the oral treatment protection operation device of the present disclosure, the operation holes have a certain limitation to the hands of the doctor for operating, in order to solve the problem that the hands for operation cannot move flexibly, the operation holes are designed on the arc-shaped sliding plates, and the arc-shaped sliding plates can slide on the operation windows of the protective cover, thus making the hands of the doctor have larger movement range in the course of treatment and making the treatment operation more flexible.

5. In accordance with the oral treatment protection operation device of the present disclosure, the soft sealing sleeve in butt-joint with the mouth is in detachable connection with the protective cover, and the soft sealing sleeve can be made into various models with different sizes to adapt to different patients.

6. In accordance with the oral treatment protection operation device of the present disclosure, the mouth mirror and the weak suction pipe can enter the protective cover through the first side pipe and the second side pipe in the course of treatment, and the first side pipe and the second side pipe can be sealed by clamps when the mouth mirror and the weak suction pipe are not used, thus preventing the aerosol and droplets from escaping; and the first side pipe and the second pipe can also be used as air inlet holes to balance the air pressure in the protective cover.

DETAILED DESCRIPTION OF THE PREFERRED EMBODIMENTS

Figure 1:
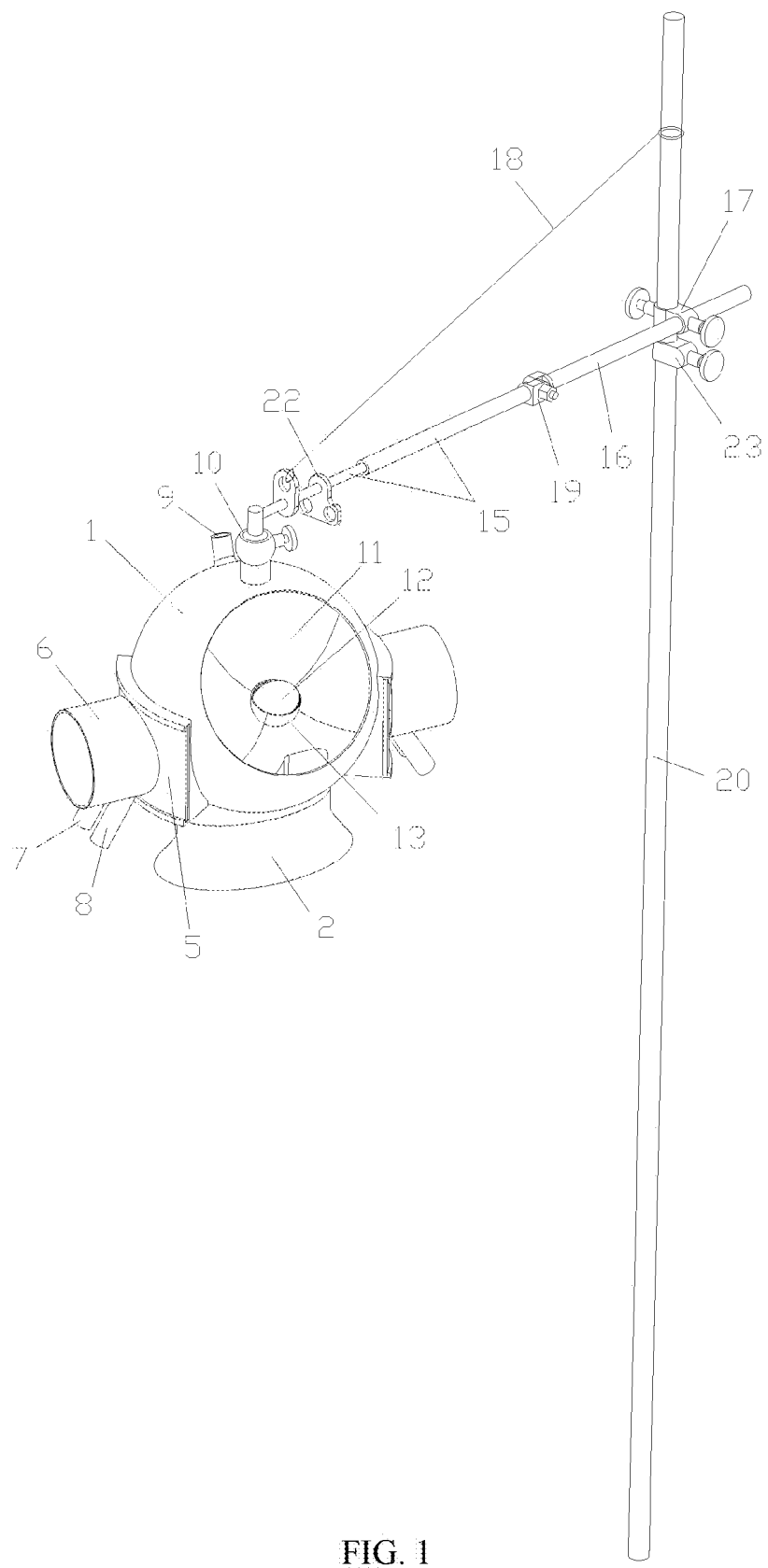
FIG. 1 is a three-dimensional structure diagram of an oral treatment protective operation device.
Figure 2:
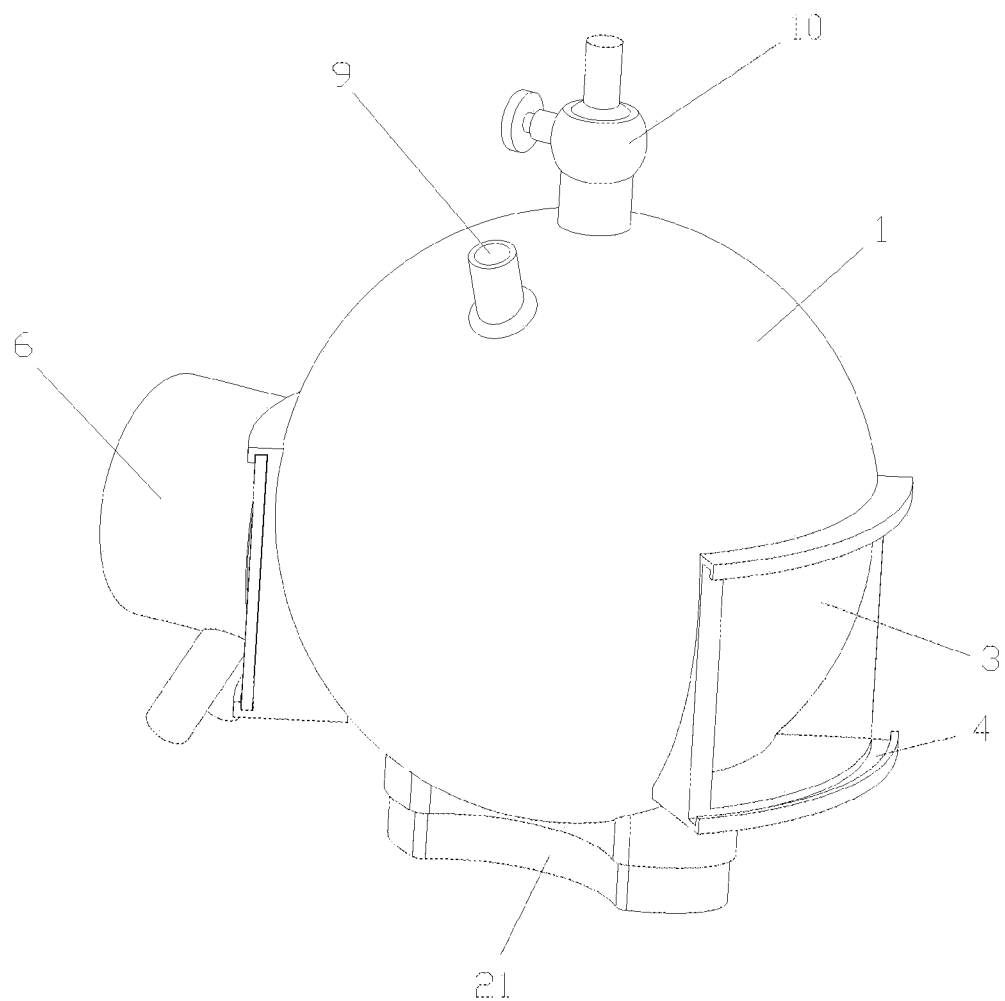
FIG. 2 is a diagram of one side of the protective cover assembly away from an operator.
Figure 3:
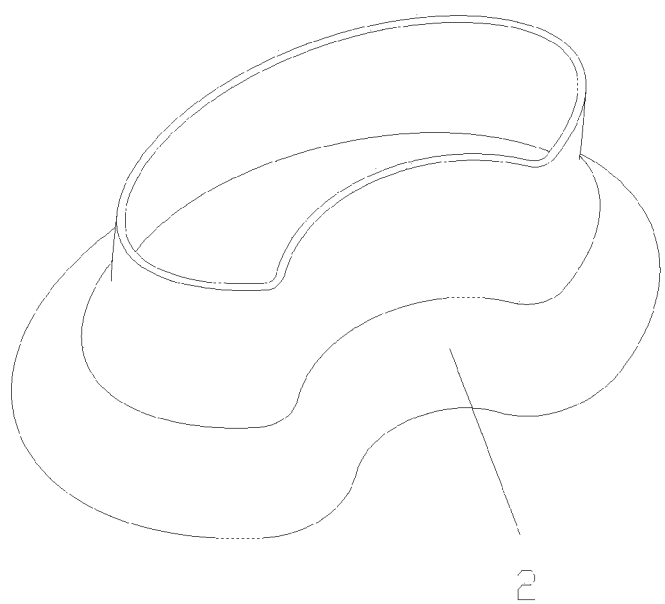
FIG. 3 is a three-dimensional structure diagram of a soft sealing sleeve in butt-joint with a mouth.
Figure 4:
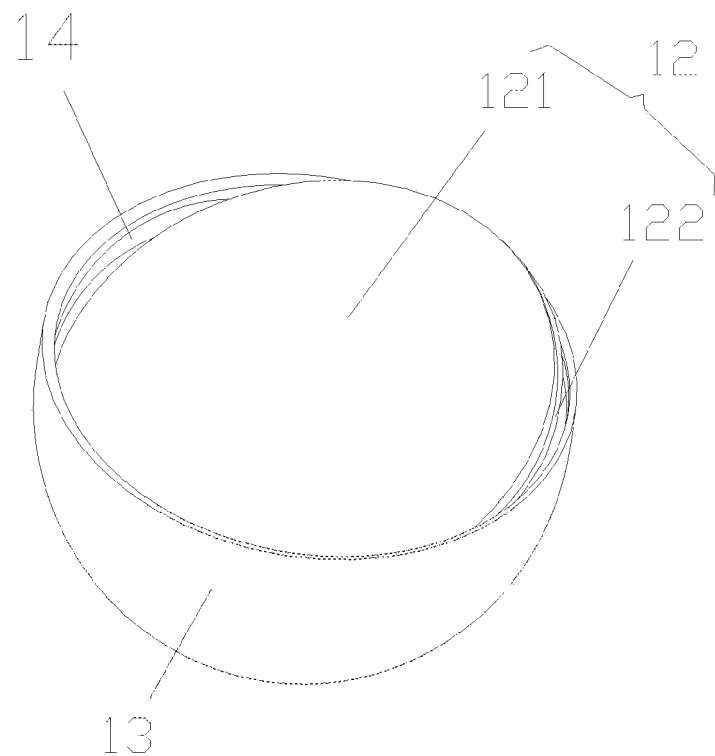
FIG. 4 is a diagram of a connecting structure of a magnifying lens and a hemispherical recess.
Figure 5:
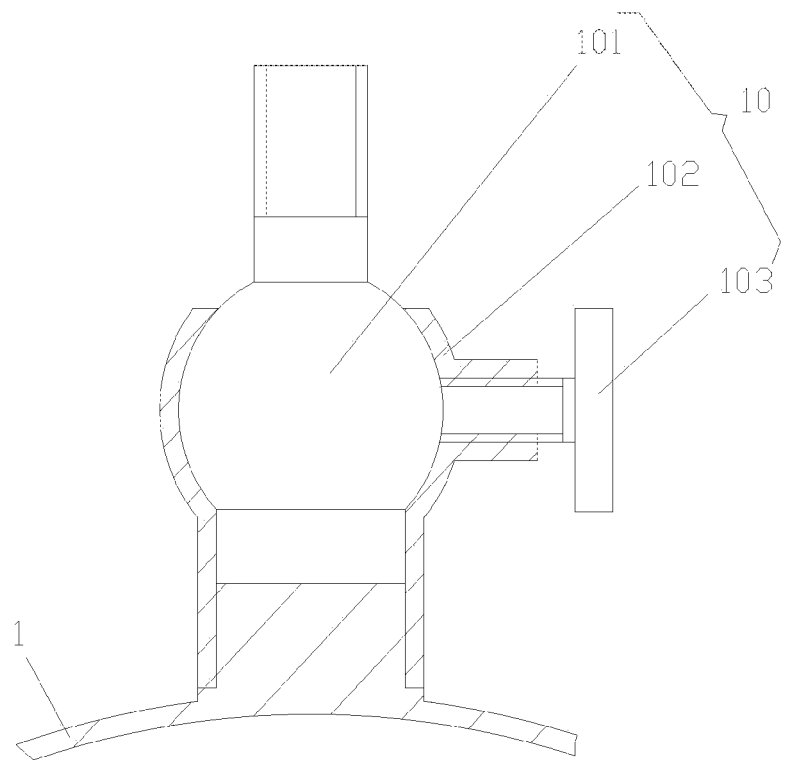
FIG. 5 is a structure diagram of a spherical hinge with a locking mechanism.
Figure 6:
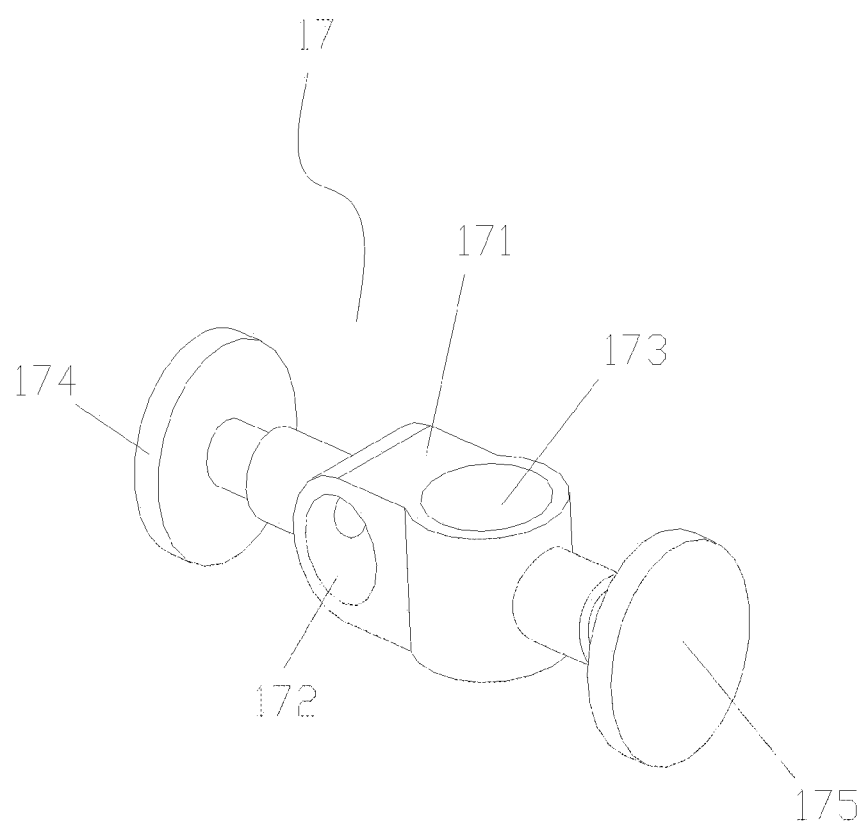
FIG. 6 is a three-dimensional structure diagram of a connecting lock sleeve.

The present disclosure is further described below with reference to the accompanying drawings and the embodiments.

As shown in the figures, an oral cavity treatment protective operation device of the embodiment comprises a protective cover assembly and a suspension support.

The protective cover assembly comprises a transparent protective cover 1, the lower part of the protective cover is provided with a soft sealing cover 2 in butt-joint with a patient's mouth, and one side, in contact with the upper lip, of the soft sealing sleeve 2 is provided with an arc-shaped concave part for avoiding the nose. The left side and the right side of the protective cover are provided with operation windows 3, opening parts of the operation windows are provided with arc-shaped guide grooves 4, arc-shaped sliding plates 5 in sliding fit with the guide grooves are arranged in the guide grooves, the arc-shaped sliding plates are provided with circular operation holes, and the operation holes are connected to soft arm sleeves 6. The arm sleeve is provided with a first side pipe 7 for penetrating of a mouth mirror and a second side pipe 8 for penetration of a weak suction pipe, and the protective cover is further provided with a connector 9 connecting a strong suction pipe; and the top of the protective cover is further provided with a spherical hinge 10 with a locking mechanism. The spherical hinge in the embodiment comprises a sphere 101, a spherical shell 102 in running fit with the sphere, and a threaded handle 103 arranged on the spherical shell. The spherical hinge in the embodiment is connected to the protective cover 1 through the spherical shell 102, and the sphere 101 is connected to the suspension support through a connecting rod. A position of the protective cover can be conveniently adjusted through the spherical hinge, and after the protective cover is adjusted, the spherical hinge can be locked by rotating the threaded handle to make an end part thereof abut against the sphere, thus guaranteeing the stability of the position of the protective cover.

A concave part 11 which is concave towards an inner side of the protective cover is formed on the side of the protective cover facing a doctor, and a hemispherical recess 13 in which a magnifying lens 12 is arranged is further formed in the concave part, and an opening part of the hemispherical recess is provided with an annular groove 14; the magnifying lens comprises a lens body 121 and a rubber ring 122 arranged on the lens body; and the magnifying lens is connected to the annular groove through the rubber ring, and can rotate around a diameter of the annular groove.

In this embodiment, the suspension support comprises a vertical-deflection adjusting rod 15, a transverse connecting rod 16, and a connecting lock sleeve 17. The suspension support further comprises a stay cable 18, and the stay cable can certainly be replaced with a stay bar. One end of the vertical-deflection adjusting rod is connected to the spherical hinge on the protective cover, the other end of the vertical-deflection adjusting rod is connected to the transverse connecting rod through a hinge joint 19 with a locking mechanism, and the position of the protective cover can be adjusted more conveniently as an angle of the vertical-deflection adjusting rod is adjustable. The connecting lock sleeve 17 comprises a sleeve body 171 which is provided with a transverse sleeve hole 172 and a vertical sleeve hole 173, and further comprises a first threaded handle 174 arranged on the transverse sleeve hole and a second threaded handle 175 arranged on the vertical sleeve hole; the transverse connecting rod is arranged in the transverse sleeve hole and in sliding fit with the transverse sleeve hold, thus making a position of the transverse connecting rod be horizontal-adjustable; the vertical sleeve hole of the connecting lock sleeve is used for being connected to a stand column 20 of a treatment chair for stomatology department, thus the position of the suspension support can be adjusted up and down and rotated horizontally; the stay bar or the stay cable is used for connecting the vertical-deflection adjusting rod and the stand column of the treatment chair for the stomatology department, thus the structure stability of the suspension support is improved, and the suspension reliability and safety of the protective cover assembly are improved.

Certainly, in different embodiments, the vertical-deflection adjusting rod can also be a telescopic rod having a length capable of being telescopically adjusted, in this case, the transverse connecting rod is fixedly connected to the connecting lock sleeve, and the position of the protective cover can be adjusted by adjusting the length of the vertical-deflection adjusting rod.

During use of the oral treatment protection operation device of this embodiment, the protective cover assembly is connected to the suspension support, the suspension support is connected to the stand column of the treatment chair for the stomatology department, and the soft sealing sleeve of the protective cover assembly is in butt-joint with the mouth of a patient; the soft sealing sleeve is in comfortable contact with the skin around the lips without causing discomfort, and the arc-shaped concave part in the middle of one side, in contact with the upper lip, of the soft sealing cover can avoid the nose; the protective cover assembly is connected to the suspension support, thus the protective cover assembly does not cause oppression discomfort to the patient. In the course of treatment, the transparent protective cover cannot affect the visual field of a doctor, the hands of the doctor enter the protective cover from the arm sleeves at two sides of the protective cover, and the sealing is improved through the fitting of the arm sleeves and the arms; and in the course of treatment, the aerosol and droplets generated by the patient are sucked away by the strong suction pipe which is connected to the protective cover, thus solving the problem of cross infection caused by diffusion of the aerosol and droplets to the surrounding environment.

In accordance with the oral treatment protection operation device in this embodiment, the operation holes have a certain limitation to the hands of the doctor for operating, in order to solve the problem that the hand for operation cannot move flexibly, the operation holes are designed on the arc-shaped sliding plates, the arc-shaped sliding plates can slide on the operation windows of the protective cover, thus making the hands of the doctor have larger movement range in the course of treatment and making the treatment operation more flexible.

In accordance with the oral treatment protection operation device in this embodiment, the angle of the magnifying lens placed therein can be adjusted according to demands of the doctor, thus the doctor can conveniently observe internal conditions of the oral cavity clearly through the magnifying lens, and the operation visual field of the doctor is improved.

As an improvement of above embodiment, the lower part of the protective cover is provided with a tubular joint 21 in buttjoint with the soft sealing cover, and the soft sealing cover is in detachable butt-joint with the tubular butt-joint. During specific implementation, the soft sealing sleeve can be made into various models with different sizes, and the soft sealing sleeve in the corresponding model can be changed according to the patient, thus guaranteeing the comfort and the sealing performance of the fitting of the soft sealing sleeve and the oral area of the patient.

As an improvement of above embodiment, the vertical-deflection adjusting rod is further provided with a clamping plate 22 for fixing the strong suction pipe, which makes the fixation of the strong suction pipe more convenient.

As an improvement of above embodiment, the suspension support further comprises a positioning sleeve 23 used for connecting to the stand column of the treatment chair for the stomatology department and located below the connecting lock sleeve. During specific implementation, when the stay cable 18 is replaced with the stay bar, the connecting lock sleeve and the stand column 20 do not need to be locked too tightly in this case, the connecting lock sleeve is prevented from sliding downwards through the positioning sleeve 23 fixed to the stand column, the advantage of which is that the protective cover and the suspension support can be rapidly moved in a lateral direction together when the patient is uncomfortable and the protective cover needs to be moved, thus separating the protective cover from the patient.

Finally, it should be noted that the above embodiments are only used to illustrate the technical solution of the present disclosure and are not limiting. Although the present disclosure has been described in detail with reference to the preferred embodiments, it should be understood by those of ordinary skill in the art that modifications or equivalent substitutions may be made to the technical solution of the present disclosure without departing from the spirit and scope of the technical solution of the present disclosure, all of which should be encompassed in the scope of the claims of the present disclosure.

What is claimed is:

1. An oral treatment protective operation device, comprising a protective cover assembly and a suspension support;

wherein the protective cover assembly comprises a transparent protective cover, a lower part of the protective cover is provided with a soft sealing sleeve configured to abut with a patient's mouth, a left side and a right side of the protective cover are provided with operation holes for entry of hands, and the operation holes are connected to soft arm sleeves; the arm sleeves are provided with a first side pipe for penetration of a mouth mirror and a second side pipe for penetration of a weak suction pipe respectively; the protective cover is further provided with a connector connecting to a strong suction pipe; and top of the protective cover is further provided with a spherical hinge with a locking mechanism;

the suspension support comprises a vertical-deflection adjusting rod, a transverse connecting rod, and a connecting lock sleeve, and further comprises a stay bar or a stay cable; one end of the vertical-deflection adjusting rod is connected to the spherical hinge on the protective cover, and another end of the vertical-deflection adjusting rod is connected to the transverse connecting rod through a hinge joint with the locking mechanism; the connecting lock sleeve comprises a sleeve body which is provided with a transverse sleeve hole and a vertical sleeve hole; the connecting lock sleeve further comprises a first threaded handle arranged on the transverse sleeve hole and a second threaded handle arranged on the vertical sleeve hole; the transverse connecting rod is arranged in the transverse sleeve hole and in sliding fit with the transverse sleeve hole; the vertical sleeve hole of the connecting lock sleeve is configured for being connected to a stand column of a treatment chair for stomatology department; and the stay bar or the stay cable is configured for connecting the vertical-deflection adjusting rod to the stand column of the treatment chair for the stomatology department.

2. The oral treatment protective operation device according to claim 1, wherein a concave part which is concave towards an inner side of the protective cover is formed on a side of the protective cover configured to face a doctor, and a hemispherical recess in which a magnifying lens is arranged is formed in the concave part, and an annular groove is formed at an opening part of the hemispherical recess; a rubber ring is arranged on a circumferential surface of the magnifying lens, and the magnifying lens is connected to the annular groove through the rubber ring, and the magnifying lens is rotatable around a diameter of the annular groove.

3. The oral treatment protective operation device according to claim 2, wherein the lower part of the protective cover is provided with a tubular joint abutting the soft sealing sleeve, and the soft sealing sleeve is detachable from the tubular joint.

4. The oral treatment protective operation device according to claim 3, wherein the vertical-deflection adjusting rod is further provided with a clamping plate for fixing the strong suction pipe.

5. The oral treatment protective operation device according to claim 2, wherein the vertical-deflection adjusting rod is a telescopic rod having a length capable of being telescopically adjusted.

6. The oral treatment protective operation device according to claim 5, wherein the vertical-deflection adjusting rod is further provided with a clamping plate for fixing the strong suction pipe.

7. The oral treatment protective operation device according to claim 2, wherein the vertical-deflection adjusting rod is further provided with a clamping plate for fixing the strong suction pipe.

8. The oral treatment protective operation device according to claim 1, wherein each of the left side and the right side of the protective cover is provided with an operation window, an opening part of the operation window is provided with an arc-shaped guide groove, and an arc-shaped sliding plate is arranged in the guide groove, which arc-shaped sliding plate is in sliding fit with the guide groove; the operation hole on the left side of the protective cover is provided on the arc-shaped sliding plate at a left side, and the operation hole on the right side of the protective cover is provided on the arc-shaped sliding plate at a right side.

9. The oral treatment protective operation device according to claim 8, wherein the lower part of the protective cover is provided with a tubular joint abutting the soft sealing sleeve, and the soft sealing sleeve is detachable from the tubular joint.

10. The oral treatment protective operation device according to claim 9, wherein the vertical-deflection adjusting rod is further provided with a clamping plate for fixing the strong suction pipe.

11. The oral treatment protective operation device according to claim 8, wherein the vertical-deflection adjusting rod is a telescopic rod having a length capable of being telescopically adjusted.

12. The oral treatment protective operation device according to claim 11, wherein the vertical-deflection adjusting rod is further provided with a clamping plate for fixing the strong suction pipe.

13. The oral treatment protective operation device according to claim 8, wherein the vertical-deflection adjusting rod is further provided with a clamping plate for fixing the strong suction pipe.

14. The oral treatment protective operation device according to claim 1, wherein the lower part of the protective cover is provided with a tubular joint abutting the soft sealing sleeve, and the soft sealing sleeve is detachable from the tubular joint.

15. The oral treatment protective operation device according to claim 4, wherein the vertical-deflection adjusting rod is further provided with a clamping plate for fixing the strong suction pipe.

16. The oral treatment protective operation device according to claim 1, wherein the vertical-deflection adjusting rod is a telescopic rod having a length capable of being telescopically adjusted.

17. The oral treatment protective operation device according to claim 16, wherein the vertical-deflection adjusting rod is further provided with a clamping plate for fixing the strong suction pipe.

18. The oral treatment protective operation device according to claim 1, wherein the vertical-deflection adjusting rod is further provided with a clamping plate for fixing the strong suction pipe.

19. The oral treatment protective operation device according to claim 1, wherein the vertical-deflection adjusting rod is further provided with a connecting plate for the stay bar or the stay cable.

20. The oral treatment protective operation device according to claim 1, wherein the suspension support further comprises a positioning sleeve configured for connecting to the stand column of the treatment chair for the stomatology department and located below the connecting lock sleeve.

* * * * *